US009649200B2

(12) United States Patent
Wickham (10) Patent No.: US 9,649,200 B2
(45) Date of Patent: May 16, 2017

(54) SPINAL IMPLANT SYSTEM AND METHOD

(71) Applicant: Warsaw Orthopedic, Inc, Warsaw, IN (US)

(72) Inventor: Jeffrey Wickham, Hernando, MS (US)

(73) Assignee: Wasaw Orthopedic, Inc., Warsaw, IN (US)

( * ) Notice: Subject to any disclaimer, the term of this patent is extended or adjusted under 35 U.S.C. 154(b) by 1 day.

(21) Appl. No.: 14/341,931

(22) Filed: Jul. 28, 2014

(65) Prior Publication Data

US 2016/0022430 A1 Jan. 28, 2016

(51) Int. Cl.
*A61F 2/44* (2006.01)
*A61F 2/30* (2006.01)

(52) U.S. Cl.
CPC .......... *A61F 2/447* (2013.01); *A61F 2/30771* (2013.01); *A61F 2/4455* (2013.01); *A61F 2002/30176* (2013.01); *A61F 2002/30784* (2013.01); *A61F 2002/30823* (2013.01); *A61F 2002/30841* (2013.01); *A61F 2002/30904* (2013.01)

(58) Field of Classification Search
CPC .. A61F 2/30771; A61F 2/4465; A61F 2/4611; A61F 2230/0069; A61F 2230/0004; A61F 2230/0034; A61F 2002/2817; A61F 2002/2835; A61F 2002/30112; A61F 2002/30187; A61F 2002/3023; A61F 2002/30787; A61F 2002/30828; A61F 2002/3083; A61F 2002/30841; A61F 2002/30892; A61F 2002/30904; A61F 2002/4475

USPC ...................... 623/17.11–17.16; 606/246–249
See application file for complete search history.

(56) References Cited

U.S. PATENT DOCUMENTS

| 5,342,365 | A | * | 8/1994 | Waldman | ........... A61B 17/1659 407/29.1 |
|---|---|---|---|---|---|
| 5,658,334 | A | * | 8/1997 | Caldarise | ................. B22C 7/02 128/898 |
| 5,888,222 | A | | 3/1999 | Coates et al. | |
| 6,010,502 | A | | 1/2000 | Bagby | |
| 6,447,544 | B1 | | 9/2002 | Michelson | |
| 6,482,233 | B1 | | 11/2002 | Aebi et al. | |
| 6,520,993 | B2 | | 2/2003 | James et al. | |
| 7,238,203 | B2 | * | 7/2007 | Bagga | ..................... A61F 2/442 623/17.11 |
| 7,615,077 | B2 | | 11/2009 | Melkent et al. | |
| 7,850,736 | B2 | | 12/2010 | Heinz | |
| 7,875,080 | B2 | * | 1/2011 | Puno | ................... A61F 2/30771 623/17.16 |
| 8,979,934 | B2 | * | 3/2015 | Kirschman | ......... A61F 2/30771 623/17.11 |
| 9,132,021 | B2 | * | 9/2015 | Mermuys | .............. A61F 2/4611 |

(Continued)

OTHER PUBLICATIONS

International Search Report issued in PCT/US2015/039201 (Foreign counterpart of the present application) mailed on Oct. 5 2015 from Korean Patent Office.

*Primary Examiner* — Pedro Philogene (57) ABSTRACT

A spinal implant comprises a body including a first vertebral engaging surface and a second vertebral engaging surface. At least one of the surfaces includes at least one tissue penetrating member. The at least one member includes a cutting surface and a guide surface that defines a cavity configured for disposal of tissue. Systems and methods of use are disclosed.

20 Claims, 10 Drawing Sheets

(56) References Cited

U.S. PATENT DOCUMENTS

| | | |
|---|---|---|
| 2005/0038511 A1 | 2/2005 | Martz et al. |
| 2013/0030529 A1* | 1/2013 | Hunt .................. A61F 2/30771 623/16.11 |
| 2013/0304211 A1* | 11/2013 | Trautwein ............. A61F 2/4455 623/17.15 |

* cited by examiner

SPINAL IMPLANT SYSTEM AND METHOD

TECHNICAL FIELD

The present disclosure generally relates to medical devices for the treatment of musculoskeletal disorders, and more particularly to a surgical system and method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, laminectomy and implantable prosthetics. As part of these surgical treatments, spinal constructs, such as, for example, bone fasteners, spinal rods and interbody devices can be used to provide stability to a treated region. For example, during surgical treatment, interbody implants can be delivered to a surgical site for fixation with bone to immobilize a joint. This disclosure describes an improvement over these prior art technologies.

SUMMARY

In one embodiment, a spinal implant is provided that comprises a body including a first vertebral engaging surface and a second vertebral engaging surface. At least one of the surfaces includes at least one tissue penetrating member. The at least one member includes a cutting surface and a guide surface that defines a cavity configured for capture of tissue. In some embodiments, systems and methods are provided.

BRIEF DESCRIPTION OF THE DRAWINGS

The present disclosure will become more readily apparent from the specific description accompanied by the following drawings, in which.

DETAILED DESCRIPTION

The exemplary embodiments of the surgical system and related methods of use disclosed are discussed in terms of medical devices for the treatment of musculoskeletal disorders and more particularly, in terms of a surgical system including a spinal implant and a method for treating a spine. In one embodiment, the systems and methods of the present disclosure are employed with a spinal joint fusion, for example, with a cervical, thoracic, lumbar and/or sacral region of a spine. In one embodiment, the spinal implant includes an interbody device, a plate and/or bone fasteners.

In some embodiments, the present system comprises a spinal implant including undercut and/or through-cut teeth. In some embodiments, the spinal implant comprises a titanium implant. In some embodiments, the spinal implant includes rasp-like teeth that may be efficiently manufactured using additive manufacturing techniques. In some embodiments, the spinal implant includes specialized undercut teeth that may be efficiently manufactured using additive manufacturing techniques.

In some embodiments, the through-cut teeth and/or the rasp-like features of the spinal implant encourage bony ongrowth. In some embodiments, the present system reduces the time for a solid spinal fusion to form. In some embodiments, the spinal implant fuses the bones to contacting surfaces of the implant. In some embodiments, the spinal implant comprises an interbody spacer designed to fuse between bone and an implant surface. In some embodiments, the spinal implant increases fusion rate by employing a rasp-like action with anchoring loops. In some embodiments, the spinal implant includes rasp-like features to collect bone dust during the implant's placement. In some embodiments, the spinal implant includes funnel-shaped surfaces under cutting tips to direct the bone dust downward into tunnels or undercuts. In some embodiments, the spinal implant guides the bone dust, which will act as seed material for new bone formation. In some embodiments, the spinal implant comprises tunnels or undercuts that travel under the cutting tips to provide positive mechanical locking of the implant to the bone.

In some embodiments, the spinal implant comprises undercut teeth to encourage bony ongrowth. In some embodiments, the spinal implant includes a surface with undercuts for bony ingrowth so that the implant is eventually mechanically locked in place. In some embodiments, the spinal implant includes an interbody spacer with surface undercuts disposed in a mirrored pattern of angled pins. In some embodiments, the spinal implant includes pins formed inexpensively with metal injection molding technology. In some embodiments, the pins are angled protruding in two directions such that bony ingrowth prevents all movement. In some embodiments, the pins are aligned at a compound angle to provide a rasp-like action. In some embodiments, the spinal implant is inserted such that the rasp-like shape shaves off bony material and pushes it down in between the pins. In some embodiments, the bony material acts as seed material for new bone formation.

In some embodiments, the spinal implant is manufactured with a rough surface finish that provides good texture for bony ongrowth. In some embodiments, the spinal implant includes a matrix of rasp-like points on the implant surface. In some embodiments, the spinal implant includes a small overlap between points to strengthen the matrix. In some embodiments, the spinal implant includes a curved cutting surface to provide prominence to the cutting points. In some embodiments, the spinal implant includes angled cutting surfaces and a funnel to direct material down into tunnel regions of the matrix. In some embodiments, the spinal implant includes rasp-like points. In some embodiments, the spinal implant includes cutting points that are offset. In some embodiments, the spinal implant includes tunnels disposed under the cutting points. In some embodiments, the spinal implant includes a curved surface that provides prominence to the cutting points. In one embodiment, the teeth include a rasp feature incorporated onto the teeth crests.

In some embodiments, the spinal implant comprises a titanium interbody spacer with an undercut surface that enables bony ingrowth. In some embodiments, the spinal implant includes a series of angled holes. In some embodiments, the spinal implant includes depression penetrating members.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, muscle, ligaments, tendons, cartilage and/or bone unless specifically referred to otherwise.

Figure 1:
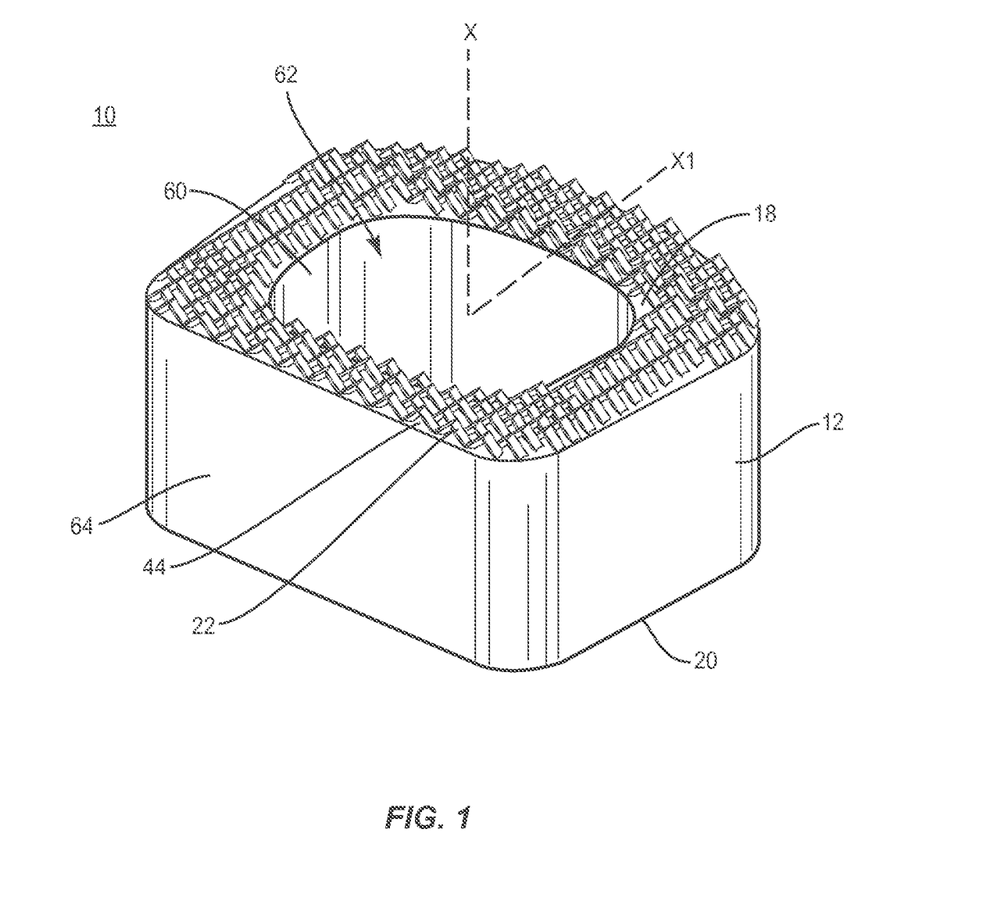
FIG. 1 is a perspective view of components of one embodiment of a system in accordance with the principles of the present disclosure.
Figure 2:
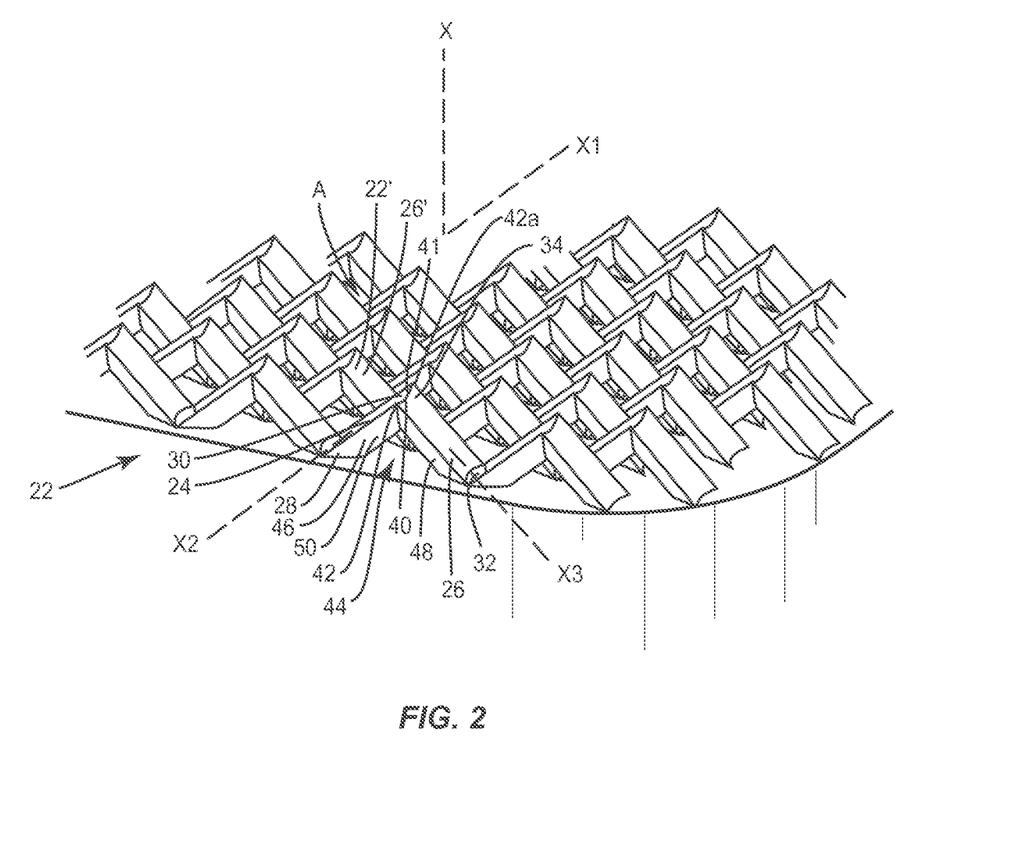
FIG. 2 is an enlarged break away view of the components shown in FIG. 1.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1 and 2, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, superelastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalciurn phosphate, or fluorapatite, tri-calcium phosphate (TOP), HA-TOP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein. In one embodiment, a spinal implant, as described herein, may be formed substantially of a biocompatible metal, such as titanium and selectively coated with a bone-growth promoting material, such as HA. In one embodiment, a spinal implant, as described herein, may be formed substantially of a biocompatible polymer, such as PEEK, and selectively coated with a biocompatible metal, such as titanium, or a bone-growth promoting material, such as HA. In some embodiments, titanium may be plasma sprayed onto surfaces of the spinal implant to modify a radiographic signature of the spinal implant and/or improve bony ongrowth to the spinal implant by application of a porous or semi-porous coating of titanium.

Spinal implant system 10 may be employed, for example, with minimally invasive procedures, including percutaneous techniques, mini-open surgical techniques and/or open surgical techniques to deliver and introduce instrumentation and/or implants, such as, for example, an interbody implant, at a surgical site within a subject body of a patient, which includes, for example, a spine. In some embodiments, the implant can include spinal constructs including one or more bone fasteners, spinal rods, connectors and/or plates. In some embodiments, various components of spinal implant system 10 may be utilized in open or traditional spinal surgical techniques.

Spinal implant system 10 includes an interbody implant 12. Implant 12 has an implant body that defines a longitudinal axis X and an axis X1 disposed perpendicular to axis X. The body extends between a vertebral engaging surface 18 and a vertebral engaging surface 20. In some embodiments, surface 18 and/or surface 20 may be rough, textured, porous, semi-porous, dimpled, knurled, toothed, grooved and/or polished to facilitate engagement with tissue. In some embodiments, the vertebral tissue may include intervertebral tissue, endplate surfaces and/or cortical bone. At least one of engaging surfaces 18, 20 includes a tissue penetrating member, such as, for example, a tooth 22. In one embodiment, implant 12 includes a plurality of teeth 22 disposed along engaging surface 18 and/or surface 20, as shown in FIG. 1. In some embodiments, teeth 22 form a rasp-like configuration along engaging surface 18 and/or surface 20. In one embodiment, teeth 22 may have various configurations, for example, round, oval, rectangular, polygonal, irregular, tapered, offset, staggered, uniform and non-uniform.

Each tooth 22 includes a portion 24 defining an axis X2 and a portion 26 defining an axis X3. Axes X2, X3 are disposed transverse to axis X and axis X1. Portion 24 extends between an end 28 and an end 30. Portion 26 extends between and end 32 and an end 34. Ends 28, 32 are connected with surface 18 and/or surface 20. Ends 28, 32 extend at an angle from surface 18 to form a cutting surface 40 at the connection of ends 30, 34. Surface 40 is configured to engage endplate tissue, such as, for example, soft tissues, bone and/or fluids to cut, shave, shear, incise and/or remove such tissue. Surface 40 includes a cutting tip, such as, for example, an arcuate concave cutting tip 41. Surface 40 includes at least one cutting point 42. As shown in FIG. 2, tip 26 extends between two cutting points 42, 42a. The arcuate shape of tip 41 is configured for creating more prominent points 42, 42a to facilitate cutting of tissue.

In some embodiments, all or a portion of cutting tip 41 may have various configurations, such as, for example, cylindrical, round, oval, oblong, triangular, polygonal having planar or arcuate side portions, irregular, uniform, non-uniform, consistent, variable, horseshoe shape, U-shape or kidney bean shape. In some embodiments, surface 40 may be rough, textured, porous, semi-porous, dimpled, knurled, toothed, grooved and/or polished to facilitate engagement and cutting of tissue.

Portion 24 and portion 26 include an undercut surface that defines a tunnel 44. Portion 24 forms a guide surface 46 that guides, drives and/or directs the tissue cut by surface 40, and/or other tissue and bone growth promoting material into an adjacent tunnel 44. Surface 46 is disposed at an angle relative to axis X2 to guide, drive and/or direct movement of tissue beneath the undercut surface of tooth 22, as described herein.

Portion 26 forms a guide surface 48 that guides, drives and/or directs the tissue cut by surface 40, and/or other tissue and bone growth promoting material into an adjacent tunnel 44. Surface 48 is disposed at an angle relative to axis X3 to guide, drive and/or direct movement of tissue beneath the undercut surface of tooth 22, as described herein. Surfaces 46, 48 are configured to form a guide surface, such as, for example, a funnel 50 therebetween. Funnel 50 is configured to guide, drive and/or direct osteogenic tissue, as described herein, into tunnel 44 to orient tissue on, adjacent and about each tooth 22, and/or collectively on, adjacent and about teeth 22, to facilitate fusion and locking of surface 18 and/or surface 20 with tissue, such as, for example, a vertebral endplate. In one embodiment, teeth 22 are disposed in an overlapping configuration, along axis X1, such that portion 24 of a first tooth 22 overlaps portion 26' of a second tooth 22', as shown in FIG. 2. In some embodiments, teeth 22 may be disposed in a rasp, offset, staggered, serial and/or overlapping configuration to provide a matrix of teeth 22. In some embodiments, teeth 22 form a lattice and/or latticework along surface 18 and/or surface 20. In some embodiments, teeth 22 are disposed along surface 18 and/or surface 20 such that cut osteogenic tissue and/or other bone growth promoting material create a mechanical interlock of implant 12 with a vertebral endplate and/or form a scaffold for bone growth.

Implant 12 includes an inner surface 60 that defines an opening 62 configured to receive an agent, which may include bone graft (not shown) and/or other materials, as described herein, for employment in a fixation or fusion treatment. In some embodiments, the cross-section geometry of implant 12 may have various configurations, such as, for example, cylindrical, round, oval, oblong, triangular, polygonal having planar or arcuate side portions, irregular, uniform, non-uniform, consistent, variable, horseshoe shape, U-shape or kidney bean shape. Implant 12 includes an outer surface 64 that is smooth or even. In some embodiments, outer surface 64 may be textured, rough, porous, semi-porous, dimpled and/or polished.

Figure 3:
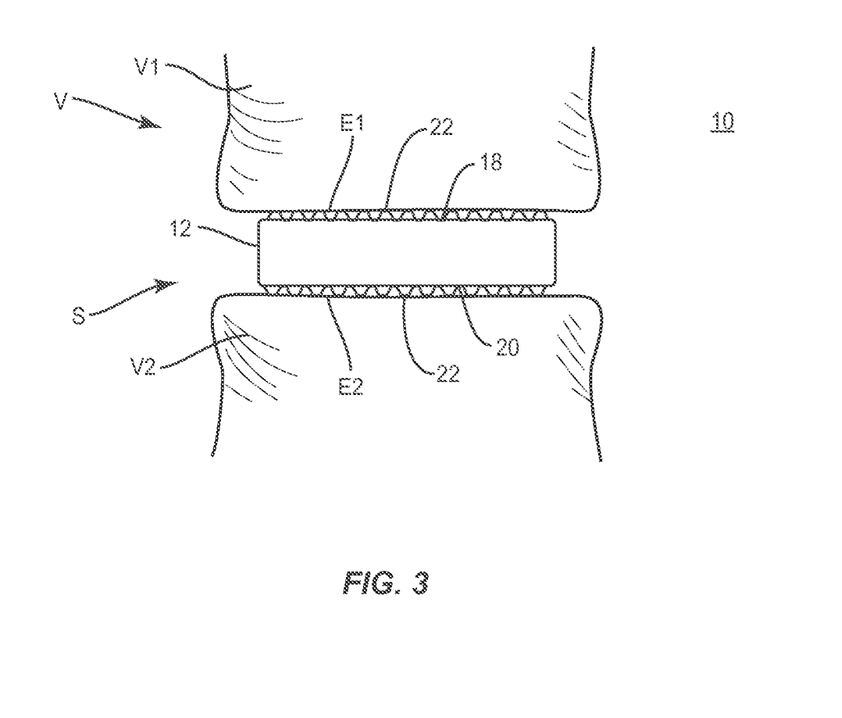
FIG. 3 is a side view of the components shown in FIG. 1 disposed with vertebrae.

In assembly, operation and use, as shown in FIG. 3, spinal implant system 10, similar to the systems and methods described herein, is disposed with tissue, such as, for example, vertebrae V, as shown in FIG. 3, for treatment of a spinal disorder, such as those described herein, affecting a section of a spine of a patient. Spinal implant system 10 may also be employed with other surgical procedures.

To treat the affected section of vertebrae V, an incision is made with a surgical instrument, such as, for example, a scalpel. In some embodiments, a discectomy is performed adjacent the intervertebral space. In some embodiments, sequential trial implants are delivered and used to distract the intervertebral space and apply appropriate tension in the intervertebral space allowing for indirect decompression. In some embodiments, the size of implant 12 is selected after trialing. In some embodiments, implant 12 is visualized by fluoroscopy and oriented before malleting into the intervertebral space.

An inserter is connected with implant 12 to direct implant 12 between vertebrae V1, V2 such that surface 18 is disposed in a cephalad orientation of the body and surface 20 is disposed in a caudal orientation of the body. The inserter delivers implant 12 through the incision to a surgical site for implantation into the intervertebral space S between vertebrae V1, V2. As implant 12 is inserted into space S, teeth 22 translate along the surface of endplate E1 and/or endplate E2. Translation of teeth 22 along the surfaces of endplate E1 and/or endplate E2 cause surface 41 and cutting points 42, 42a to engage the soft tissues, bone and/or fluids of endplate E1 and/or endplate E2 to cut, shave, shear, incise and/or remove such tissue from the surface of endplate E1 and/or endplate E2 to collect osteogenic tissue, such as, for example, bone dust. The matrix of teeth 22 causes the bone dust to be disposed on, adjacent and about the surfaces of each tooth 22 and collectively teeth 22.

Funnel 50 guides, drives and/or directs the bone dust downward and axially in the direction of axis X2, as shown by arrow A in FIG. 2, into tunnel 40 and on, adjacent and about the surfaces of each tooth 22 and collectively teeth 22. In some embodiments, movement of the bone dust into tunnel 40 causes the bone dust to act as seed material to facilitate new bone formation causing a positive mechanical lock of implant 12 to vertebrae V1, V2. In an implanted position, as shown in FIG. 3, surface 20 engages endplate tissue of endplate E1 and surface 18 engages endplate tissue E2.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiopaque markers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10. In some embodiments, spinal implant system 10 may include one or a plurality of plates, connectors and/or bone fasteners for use with a single vertebral level or a plurality of vertebral levels.

In one embodiment, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

Figure 4:
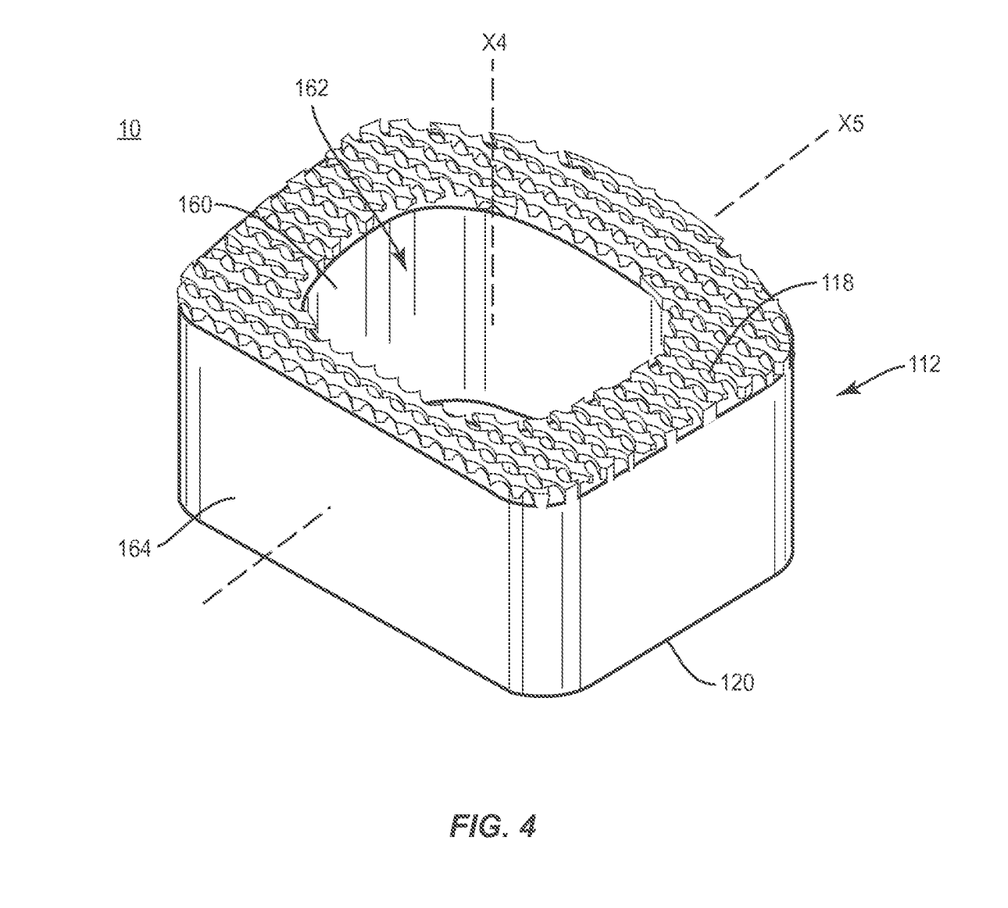
FIG. 4 is a perspective view of components of one embodiment of a system in accordance with the principles of the present disclosure.
Figure 5:
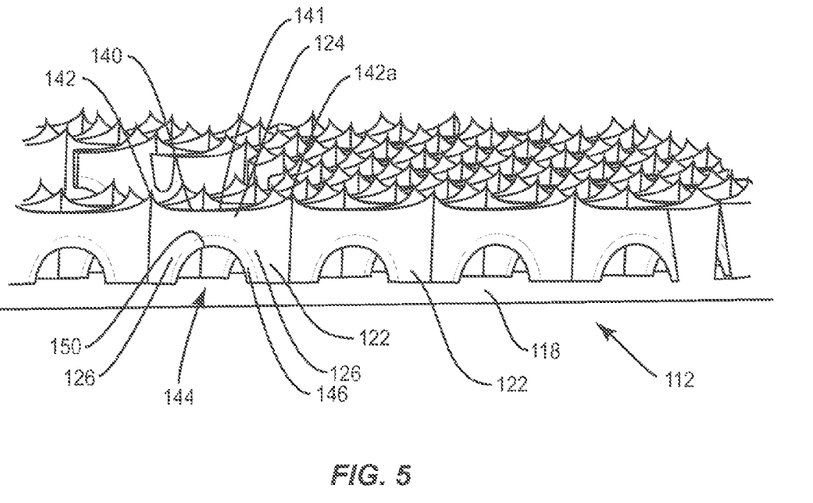
FIG. 5 is an enlarged break away view of the components shown in FIG. 4.
Figure 6:
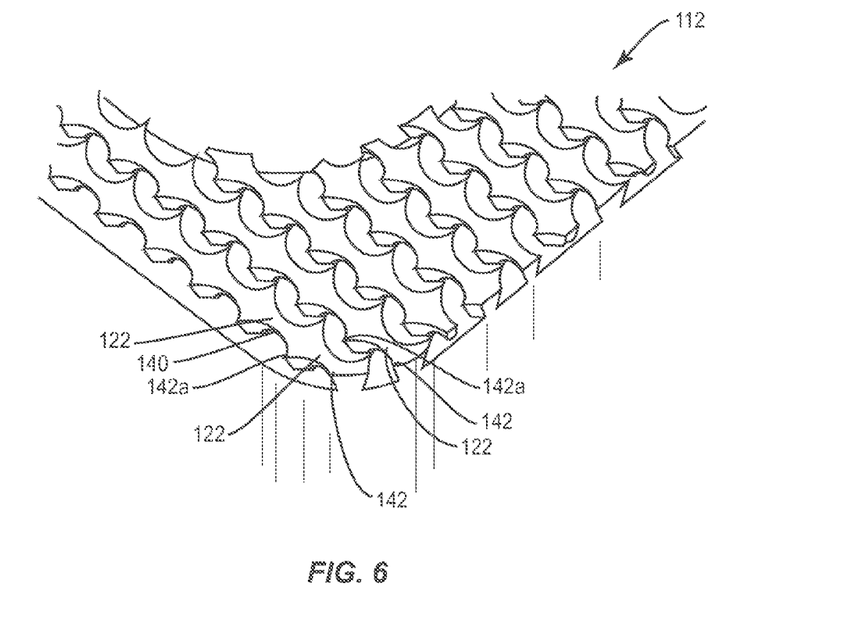
FIG. 6 is an enlarged break away view of the components shown in FIG. 4.

In one embodiment, as shown in FIGS. 4-6, spinal implant system 10, similar to the systems and methods described with regard to FIGS. 1-3, includes an interbody implant 112. Implant 112, similar to implant 12 described above, has an implant body that defines a longitudinal axis X4 and an axis X5. The implant body of implant 112 extends between a vertebral engaging surface 118 and a vertebral engaging surface 120. At least one of engaging surfaces 118, 120 includes a penetrating member, such as, for example, a tooth 122. In one embodiment, implant 112 includes a plurality of teeth 122 disposed along engaging surface 118 and/or surface 120, as shown in FIG. 4, forming a rasp-like configuration. In some embodiments, surface 118 and/or surface 120 may include one or a plurality of teeth 122.

Each tooth 122 includes an arch 124 and a pair of legs 126. Legs 126 are connected with surface 118 and/or surface 120. Legs 126 extend from surface 118 and/or surface 120 to arch 124 and arch 124 extends therefrom to form a cutting surface 140, similar to cutting surface 40 described herein. Surface 140 is configured to engage endplate tissue, such as, for example, soft tissues, bone and/or fluids to cut, shave, shear, incise and/or remove such tissue. Surface 140 includes a cutting tip, such as, for example, an arcuate concave cutting tip 141. Surface 140 includes at least one cutting point 142. As shown in FIG. 5, tip 141 extends between two cutting points 142, 142a. The arcuate shape of tip 141 is configured for creating more prominent points 142, 142a to facilitate cutting of tissue.

Arch 124 and legs 126 include an undercut surface that defines a tunnel 144. Arch 124 and legs 126 form a guide surface 146 that guides, drives and/or directs the tissue cut by surface 140, and/or other tissue and bone growth promoting material into an adjacent tunnel 144. Surface 146 has an arcuate and/or concave configuration to guide, drive and/or direct movement of tissue beneath the undercut surface of tooth 122, as described herein.

Surface 146 is configured to form a guide surface, such as, for example, a funnel 150. Funnel 150 is configured to guide, drive and/or direct osteogenic tissue, as described herein, into tunnel 144 to orient tissue on, adjacent and about each tooth 122, and/or collectively on, adjacent and about teeth 122, to facilitate fusion and locking of surface 118 and/or surface 120 with tissue, such as, for example, a vertebral endplate. In some embodiments, teeth 122 are disposed in a serial configuration such that teeth 122 form linear rows along surface 118 and/or surface 120. In some embodiments, each linear row is monolithically formed. In some embodiments, teeth 122 and/or rows of teeth 122 may be disposed in a rasp, offset, staggered, serial and/or overlapping configuration to provide a matrix of teeth 122. In some embodiments, teeth 122 form a lattice and/or latticework along surface 118 and/or surface 120. In some embodiments, teeth 122 are disposed along surface 118 and/or surface 120 such that the cut osteogenic tissue and/or other bone growth promoting material create a mechanical interlock of implant 112 with a vertebral endplate and/or form a scaffold for bone growth.

Implant 112 includes an inner surface 160 that defines an opening 162 configured to receive an agent, which may include bone graft (not shown) and/or other materials, as described herein, for employment in a fixation or fusion treatment. Implant 112 includes an outer surface 164 that is smooth or even.

Figure 7:
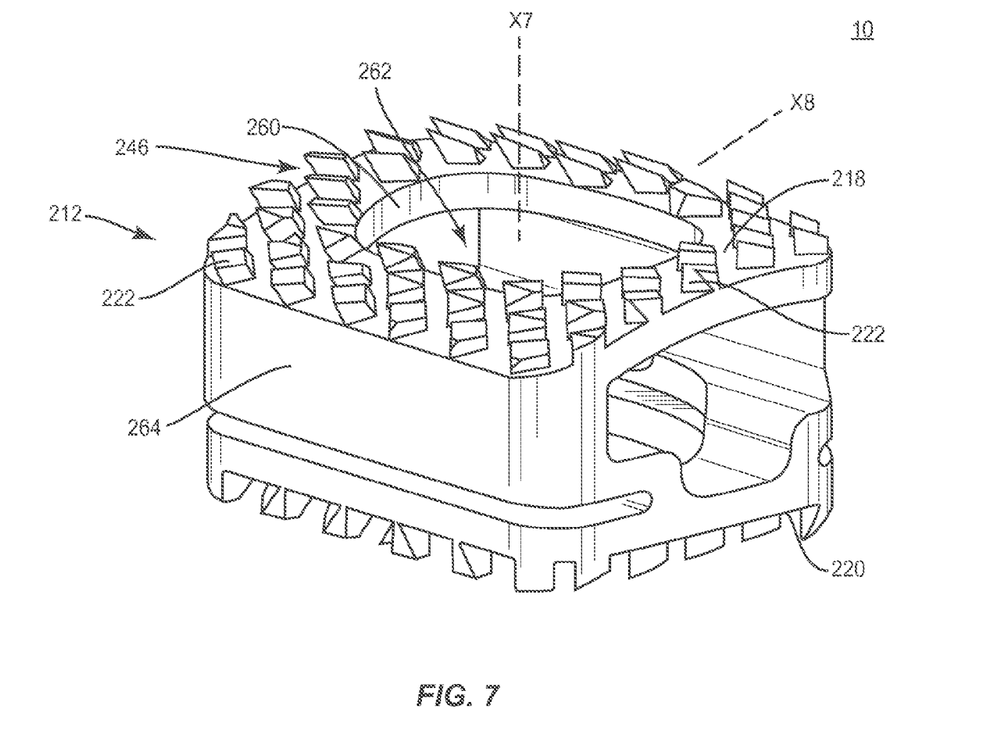
FIG. 7 is a perspective view of components of one embodiment of a system in accordance with the principles of the present disclosure.
Figure 8:
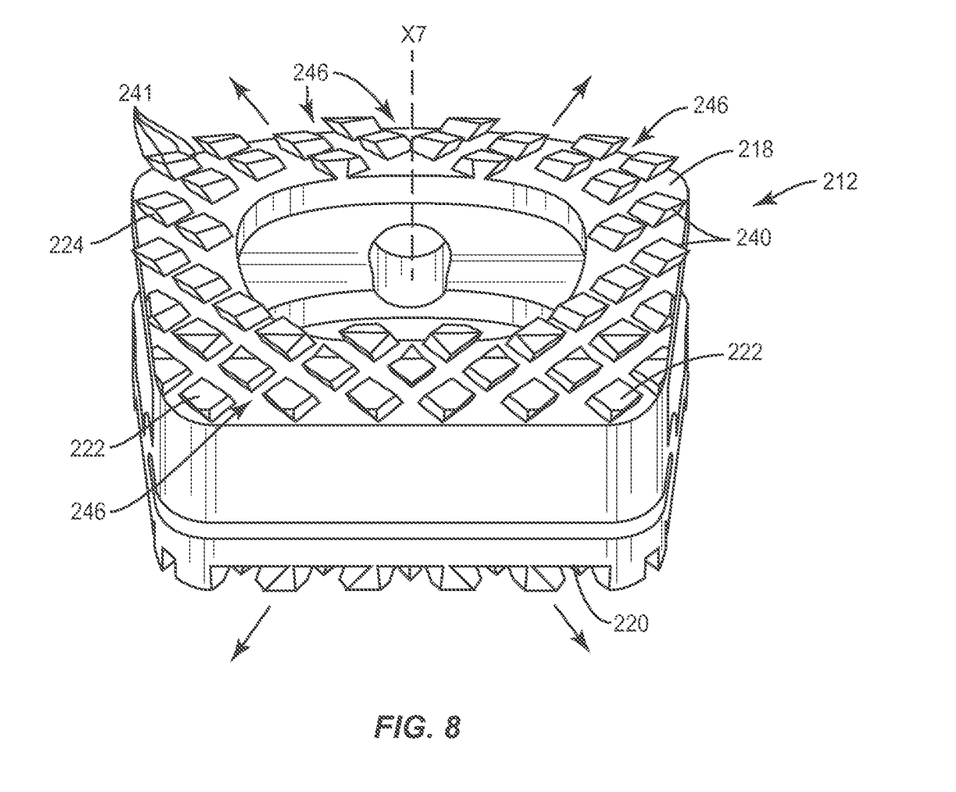
FIG. 8 is a perspective view of the components shown in FIG. 7.
Figure 9:
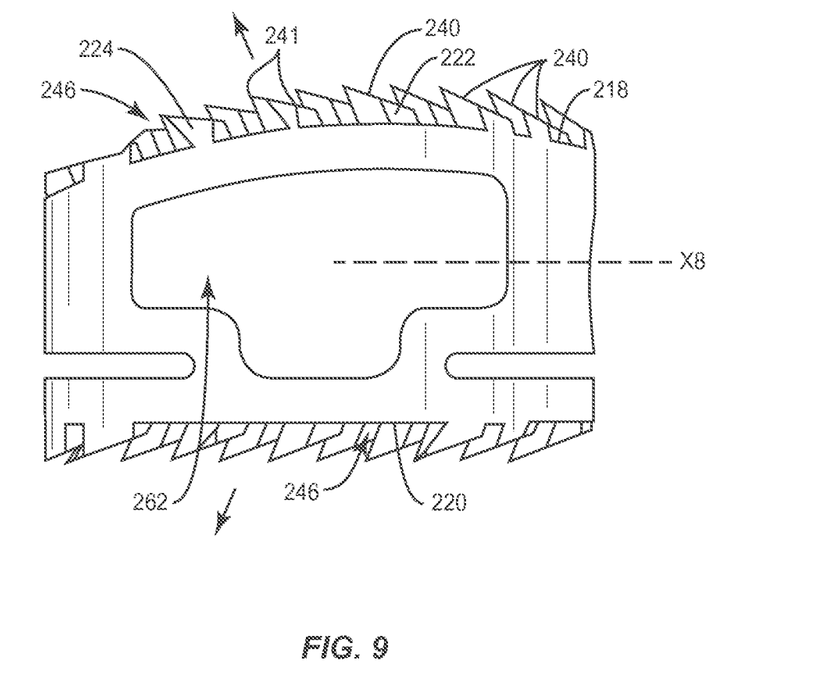
FIG. 9 is a side view of the components shown in FIG. 7.

In one embodiment, as shown in FIGS. 7-9, spinal implant system 10, similar to the systems and methods described herein, includes an interbody implant 212, similar to implant 12 described herein. Implant 212 has an implant body that defines a longitudinal axis X7 and an axis X8. The implant body of implant 212 extends between a vertebral engaging surface 218 and a vertebral engaging surface 220. At least one of engaging surfaces 218, 220 includes a tissue penetrating member, such as, for example, an angled cutting pin 222. In some embodiments, implant 212 can include one or a plurality of pins 222 disposed along engaging surface 218 and/or surface 220.

Each pin 222 includes sidewalls 224 connected with surface 218 and/or surface 220. Sidewalls 224 extend from surface 218 and/or surface 220 to form cutting surfaces, such as, for example, cutting edges 240, similar to cutting surface 40 described herein, disposed about pin 222. In some embodiments, each pin 222 includes four cutting edges 240. Each edge 240 is configured to engage endplate tissue, such as, for example, soft tissues, bone and/or fluids to cut, shave, shear, incise and/or remove such tissue. Edges 240 form cutting points 241 about pin 222. In some embodiments, each pin 222 includes four cutting points 241.

In some embodiments, pins 222 are disposed in a mirrored pattern of angled pins. In some embodiments, pins 222 are oriented in two directions such that bony ingrowth prevents movement of implant 212 relative to an endplate surface engaged therewith. In some embodiments, pins 222 are oriented and aligned at compound angles to provide a rasp-like matrix, cutting action and/or osteogenic tissue collection, similar to that described herein. In some embodiments, pins 222 are oriented in a plurality of directions and identically disposed and/or mirrored about axes X7 and/or X8, in the directions shown by the arrows in FIGS. 8 and 9.

Pins 222 form a guide surface, such as, for example, tunnels 246 that guide, drive and/or direct tissue cut by edges 240 and points 241, and/or other tissue and bone growth promoting material into adjacent tunnels 246.

Sidewalls 224 are configured to guide, drive and/or direct osteogenic tissue, as described herein, into tunnels 246 to orient tissue on, adjacent and about each pin 222, and/or collectively on, adjacent and about pins 222, to facilitate fusion and locking of surface 218 and/or surface 220 with tissue, such as, for example, a vertebral endplate. In some embodiments, pins 222 may be disposed in a rasp, offset, staggered, serial and/or overlapping configuration to provide a matrix of pins 222. In some embodiments, pins 222 form a lattice and/or latticework along surface 218 and/or surface 220. In some embodiments, pins 222 are disposed along surface 218 and/or surface 220 such that cut osteogenic tissue and/or other bone growth promoting material create a mechanical interlock of implant 212 with a vertebral endplate and/or form a scaffold for bone growth.

Implant 212 includes an inner surface 260 that defines an opening 262 configured to receive an agent, which may include bone graft (not shown) and/or other materials, as described herein, for employment in a fixation or fusion treatment. Implant 212 includes an outer surface 264 that is smooth or even.

Figure 10:
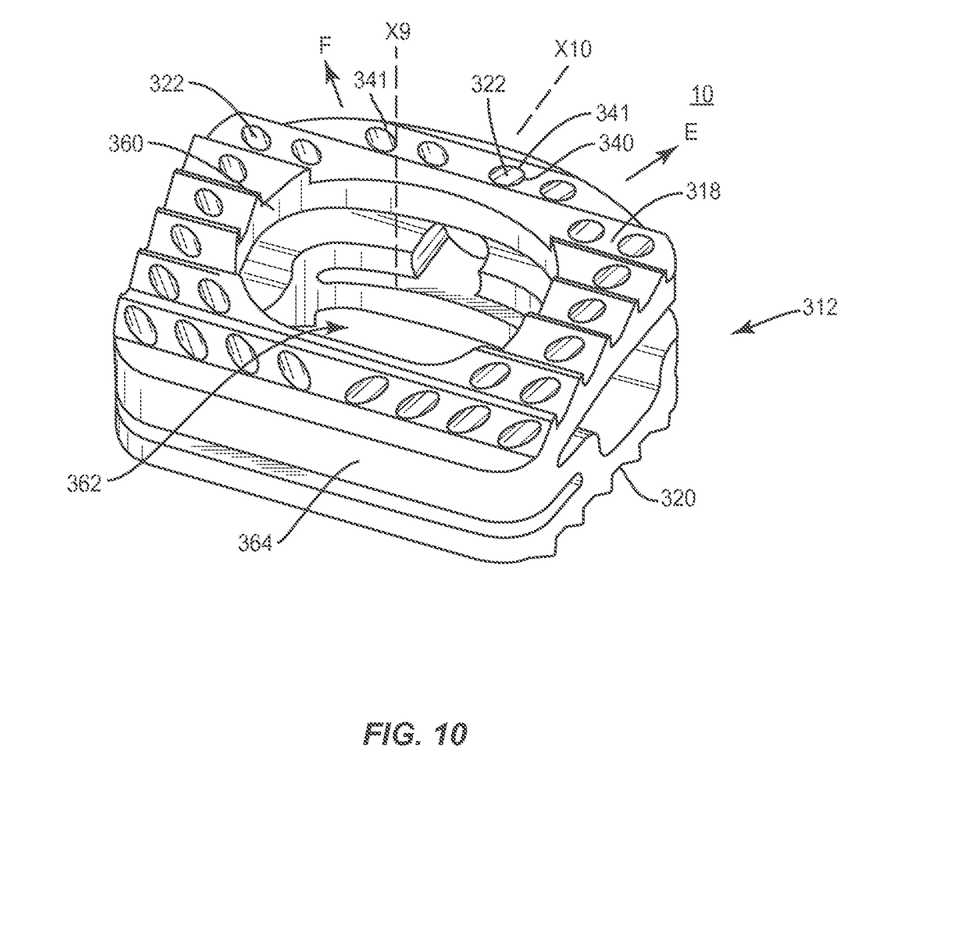
FIG. 10 is a perspective view of components of one embodiment of a system in accordance with the principles of the present disclosure.

In one embodiment, as shown in FIG. 10, spinal implant system 10, similar to the systems and methods described herein, includes an interbody implant 312, similar to implant 12 described herein. Implant 312 has an implant body that defines a longitudinal axis X9 and an axis X10. The implant body of implant 312 extends between a vertebral engaging surface 318 and a vertebral engaging surface 320. At least one of the engaging surfaces 318, 320 includes a tissue penetrating member, such as, for example, a cutting surface that defines an angled opening 322. In some embodiments, implant 312 includes one or a plurality of openings 322 disposed along engaging surface 318 and/or surface 320.

Each opening 322 is defined by a cutting surface 340. Surface 318 and/or surface 320 include a plurality of surfaces 340 that define a plurality of openings 322. Each surface 340 includes a cutting edge 341 that is configured to engage endplate tissue, such as, for example, soft tissues, bone and/or fluids to cut, shave, shear, incise and/or remove such tissue. In some embodiments, openings 322 are disposed along surface 318 and/or surface 320 such that cut osteogenic tissue and/or other bone growth promoting material create a mechanical interlock of implant 312 with a vertebral endplate and/or form a scaffold for bone growth. Openings 322 are oriented in a first direction, as shown by arrow E in FIG. 10, and a second direction, as shown by arrow F in FIG. 10.

Implant 312 includes an inner surface 360 that defines an opening 362 configured to receive an agent, which may include bone graft (not shown) and/or other materials, as described herein, for employment in a fixation or fusion treatment. Implant 312 includes an outer surface 364 that is smooth or even.

Figure 11:
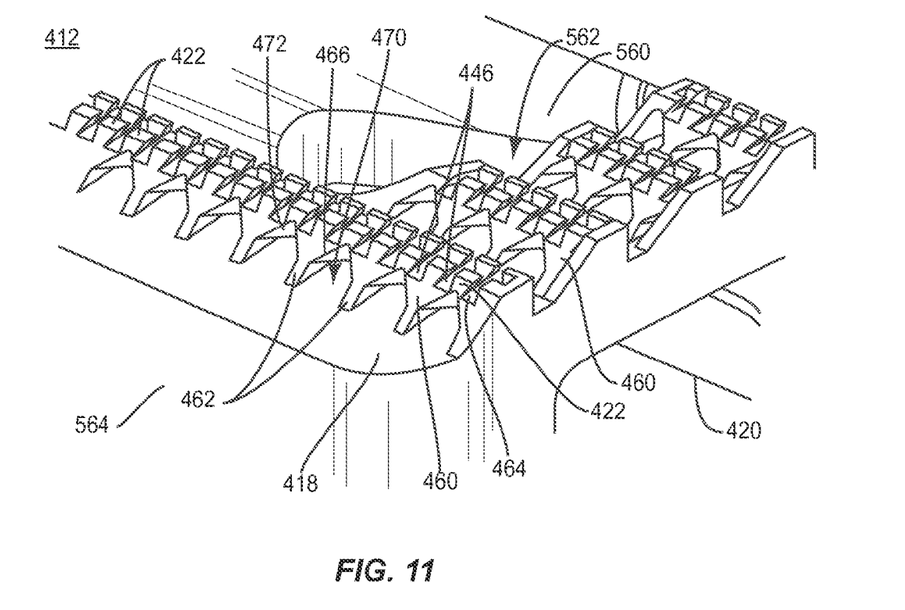
FIG. 11 is an enlarged break away view of components of one embodiment of a system in accordance with the principles of the present disclosure.
Figure 12:
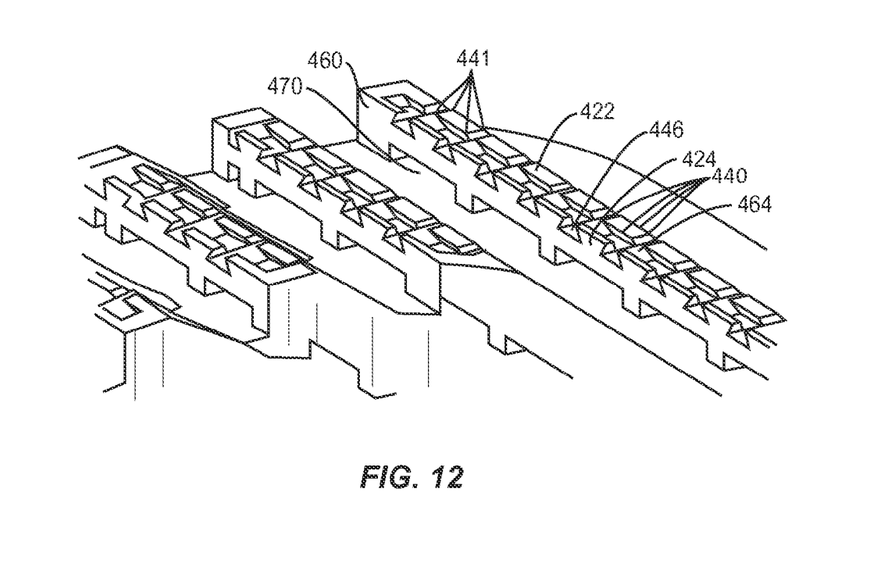
FIG. 12 is an enlarged break away view of the components shown in FIG. 11.

In one embodiment, as shown in FIGS. 11 and 12, spinal implant system 10, similar to the systems and methods described with regard to FIGS. 1-3, includes an interbody implant 412. Implant 412, similar to implant 12 described above, extends between a vertebral engaging surface 418 and a vertebral engaging surface 420. At least one of engaging surfaces 418, 420 includes a penetrating member, such as, for example, a tooth 422. In one embodiment, implant 412 includes a plurality of teeth 422 disposed along engaging surface 418 and/or surface 420, as shown in FIG. 11, forming a rasp-like configuration. In some embodiments, surface 418 and/or surface 420 may include one or a plurality of teeth 422.

Each tooth 422 includes sidewalls 424 connected with a surface 464 of an arch 460, as described herein. Sidewalls 424 extend from surface 464 to form cutting surfaces, such as, for example, cutting edges 440, similar to cutting surface 40 described herein, disposed about tooth 422. In some embodiments, each tooth 422 includes four cutting edges 440. Each edge 440 is configured to engage endplate tissue, such as, for example, soft tissues, bone and/or fluids to cut, shave, shear, incise and/or remove such tissue. Edges 440 form cutting points 441 about tooth 422. In some embodiments, each tooth 422 includes four cutting points 441.

In some embodiments, teeth 422 are oriented and aligned to provide a rasp-like matrix, cutting action and/or osteogenic tissue collection, similar to that described herein. Teeth 422 form a guide surface, such as, for example, tunnels 446 that guide, drive and/or direct tissue cut by edges 440 and points 441, and/or other tissue and bone growth promoting material into and adjacent tunnels 446.

Sidewalls 424 are configured to guide, drive and/or direct osteogenic tissue, as described herein, into tunnels 446 to orient tissue on, adjacent and about each tooth 422, and/or collectively on, adjacent and about teeth 422, to facilitate fusion and locking of plate 412 with tissue, such as, for example, a vertebral endplate. In some embodiments, teeth 422 may be disposed in a rasp, offset, staggered, serial and/or overlapping configuration to provide a matrix of teeth 422. In some embodiments, teeth 422 are disposed such that cut osteogenic tissue and/or other bone growth promoting material create a mechanical interlock of implant 412 with a vertebral endplate and/or form a scaffold for bone growth Teeth 422 are connected to a base, such as, for example, arch 460. Arch 460 includes a pair of legs 462 and surface 464. Teeth 422 are connected to and extend from surface 464. Legs 462 extend from surface 464 in a direction towards surface 418 and/or surface 420 and are connected with surface 418 and/or surface 420. Legs 462 extend from surface 418 and/or surface 420 to form arch 460. Arch 460 includes a cutting surface 466, as shown in FIG. 11. Surface 466 is configured to engage endplate tissue, such as, for example, soft tissues, bone and/or fluids to cut, shave, shear, incise and/or remove such tissue.

Arch 460 and legs 462 include an undercut surface that defines a tunnel 470. Arch 460 and legs 462 form a guide surface 472 that guides, drives and/or directs the tissue cut by surface 466, and/or other tissue and bone growth promoting material into and adjacent tunnel 470. Surface 466 has a concave configuration to guide, drive and/or direct movement of tissue beneath the undercut surface of tooth 422, as described herein.

In some embodiments, teeth 422 and arches 460 are disposed in a serial configuration such that teeth 422 and arches 460 form linear rows along surface 418 and/or surface 420. In some embodiments, each linear row is monolithically formed. In some embodiments, rows of teeth 422 and arches 460 may be disposed in a rasp, offset, staggered, serial and/or overlapping configuration to provide a matrix of teeth 422 and arches 460.

Implant 412 includes an inner surface 560 that defines an opening 562 configured to receive an agent, which may include bone graft (not shown) and/or other materials, as described herein, for employment in a fixation or fusion treatment. Implant 412 includes an outer surface 564 that is smooth or even.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant comprising:
    a body including a first vertebral engaging surface and an opposite second vertebral engaging surface,
    at least one of the surfaces including at least one tissue penetrating member extending outwardly therefrom, the at least one member including a cutting surface and a guide surface, an undercut surface of the guide surface and the engaging surface defining a tunnel therebetween such that the tunnel is positioned below the cutting surface, the tunnel being configured for disposal of tissue.

2. A spinal implant as recited in claim 1, wherein the tissue includes at least a vertebral endplate and osteogenic tissue that is disposed with the tunnel and about the at least one member to fix the engaging surface with the vertebral endplate.

3. A spinal implant as recited in claim 1, wherein the cutting surface comprises a cutting tip.

4. A spinal implant as recited in claim 1, wherein the cutting surface comprises an arcuate cutting tip.

5. A spinal implant as recited in claim 1, wherein the cutting surface comprises a cutting point.

6. A spinal implant as recited in claim 1, wherein the cutting surface comprises an arcuate cutting tip and at least one cutting point.

7. A spinal implant as recited in claim 1, wherein the undercut surface comprises at least one angled surface.

8. A spinal implant as recited in claim 1, wherein the undercut surface comprises a first angled surface and a second angled surface, the angled surfaces defining a funnel configured to guide tissue into the tunnel.

9. A spinal implant as recited in claim 1, wherein the at least one member includes a plurality of tissue penetrating members disposed along the engaging surface.

10. A spinal implant as recited in claim 9, wherein the members comprise a matrix of cutting surfaces.

11. A spinal implant as recited in claim 9, wherein the members comprise offset cutting surfaces.

12. A spinal implant as recited in claim 9, wherein the members comprise cutting surfaces including a rasp configuration.

13. A spinal implant as recited in claim 9, wherein the undercut surfaces direct tissue between the members.

14. A spinal implant as recited in claim 1, wherein the body defines a longitudinal axis and the at least one member is oriented transverse to the longitudinal axis.

15. A spinal implant as recited in claim 1, wherein the body defines a longitudinal axis and the at least one member includes a plurality of tissue penetrating members oriented in at least a first direction and a second direction, the directions being disposed transverse to the longitudinal axis.

16. A spinal implant as recited in claim 1, wherein the tunnel has a triangular cross sectional configuration.

17. A spinal implant as recited in claim 1, wherein the tunnel has a semi-circular cross sectional configuration.

18. A spinal implant as recited in claim 1, wherein the tunnel has a rectangular cross sectional configuration.

19. A spinal implant comprising:
    a body including a first vertebral engaging surface and an opposite second vertebral engaging surface, and
    at least one of the surfaces including a plurality of tissue penetrating members extending outwardly therefrom, each of the members including a cutting surface engageable with a vertebral endplate and a guide surface, an undercut surface of the guide surface and the engaging surface defining a tunnel therebetween such that the tunnel is positioned below the cutting surface, the tunnel being configured to capture osteogenic tissue in the tunnel and about the penetrating members to fix the engaging surface with the vertebral endplate.

20. A spinal implant comprising:
    a body defining a longitudinal axis and including a first vertebral engaging surface and an opposite second vertebral engaging surface,
    at least one of the engaging surfaces including a plurality of tissue penetrating members extending outwardly therefrom, the members being oriented in at least a first direction and a second direction, the directions being disposed transverse to the longitudinal axis, and
    each of the members including a cutting surface engageable with a vertebral endplate and an undercut guide surface, an undercut surface of the guide surface and the engaging surface defining a tunnel therebetween such that the tunnel is positioned below the cutting surface, the tunnel being configured to direct osteogenic tissue into the tunnel and between the penetrating members to fix the engaging surface with the vertebral endplate.

* * * * *

UNITED STATES PATENT AND TRADEMARK OFFICE
CERTIFICATE OF CORRECTION

PATENT NO. : 9,649,200 B2
APPLICATION NO. : 14/341931
DATED : May 16, 2017
INVENTOR(S) : Wickham Page 1 of 1

It is certified that error appears in the above-identified patent and that said Letters Patent is hereby corrected as shown below:

In the Specification

Column 1, Line 3, delete "HELD" and insert -- FIELD --, therefor.

Column 1, Line 52, delete "FIG. 1:" and insert -- FIG. 1; --, therefor.

Column 4, Line 57, delete "tricalciurn" and insert -- tricalcium --, therefor.

Column 4, Lines 58-59, delete "(TOP), HA-TOP," and insert -- (TCP), HA-TCP, --, therefor.

Column 6, Line 4, delete "tip 26" and insert -- tip 41 --, therefor.

Column 7, Line 23, delete "surface" and insert -- tip --, therefor.

Column 7, Line 33, delete "tunnel 40" and insert -- tunnel 44 --, therefor.

Column 7, Line 36, delete "tunnel 40" and insert -- tunnel 44 --, therefor.

Signed and Sealed this
Fourteenth Day of August, 2018

Andrei Iancu
*Director of the United States Patent and Trademark Office*